(12) United States Patent
Early et al.

(10) Patent No.: US 9,895,180 B2
(45) Date of Patent: Feb. 20, 2018

(54) ANKLE TIBIA PLATES

(71) Applicant: OsteoMed LLC, Addison, TX (US)

(72) Inventors: John Early, Dallas, TX (US); Michael E. Brage, Laguna Woods, CA (US); Gregory Pomeroy, Cape Elizabeth, ME (US); Brian Carpenter, Ft. Worth, TX (US); Douglas W. Miller, Dallas, TX (US)

(73) Assignee: OsteoMed LLC, Addison, TX (US)

( * ) Notice: Subject to any disclaimer, the term of this patent is extended or adjusted under 35 U.S.C. 154(b) by 524 days.

(21) Appl. No.: 14/279,225

(22) Filed: May 15, 2014

(65) Prior Publication Data

US 2015/0327899 A1    Nov. 19, 2015

(51) Int. Cl.
*A61B 17/80* (2006.01)

(52) U.S. Cl.
CPC .......... *A61B 17/8057* (2013.01); *A61B 17/80* (2013.01); *A61B 17/8061* (2013.01); *A61B 17/8085* (2013.01)

(58) Field of Classification Search
CPC .. A61B 17/80; A61B 17/8085; A61B 17/8061
See application file for complete search history.

(56) References Cited

U.S. PATENT DOCUMENTS

| | | | |
|---|---|---|---|
| 8,182,517 B2 | 5/2012 | Sixto, Jr. et al. | |
| 8,317,842 B2 | 11/2012 | Graham et al. | |
| 8,518,042 B2 * | 8/2013 | Winslow | A61B 17/8061 606/280 |
| 8,690,916 B2 | 4/2014 | Gonzalez-Hernandez | |
| 8,790,378 B2 | 7/2014 | Castaneda et al. | |
| 9,333,014 B2 | 5/2016 | Gonzalez-Hernandez | |
| 2008/0300637 A1 * | 12/2008 | Austin | A61B 17/74 606/290 |

* cited by examiner

*Primary Examiner* — Andrew Yang
(74) *Attorney, Agent, or Firm* — Norton Rose Fulbright US LLP

(57) ABSTRACT

Implant devices for the internal fixation of fractured bones, and more particularly to ankle plates for the tibia bone are disclosed and include an anterolateral tibia plate having an L-shaped body including a proximal portion defining a longitudinal axis, and a distal portion defining a traverse axis, and having a support bridge connected between the proximal portion and the distal portion. Implant devices disclosed also include an anterior tibia plate having an elongated first portion, a second portion that widens outward with respect to the elongated first portion, and a plurality of removable tabs attached to the outer edge of the second portion. Implant devices disclosed also include a medial tibia plate having an elongated shaft with a proximal portion and a distal portion. The distal portion is configured to extend proximate to a base of medial malleolus, and has a curvature with respect to a longitudinal axis defined by the elongated shaft. The distal portion may include a plurality of removable tabs. The removable tabs may be disposed to define an opening between the removable tabs to orient a bone fastener into a bone.

7 Claims, 8 Drawing Sheets

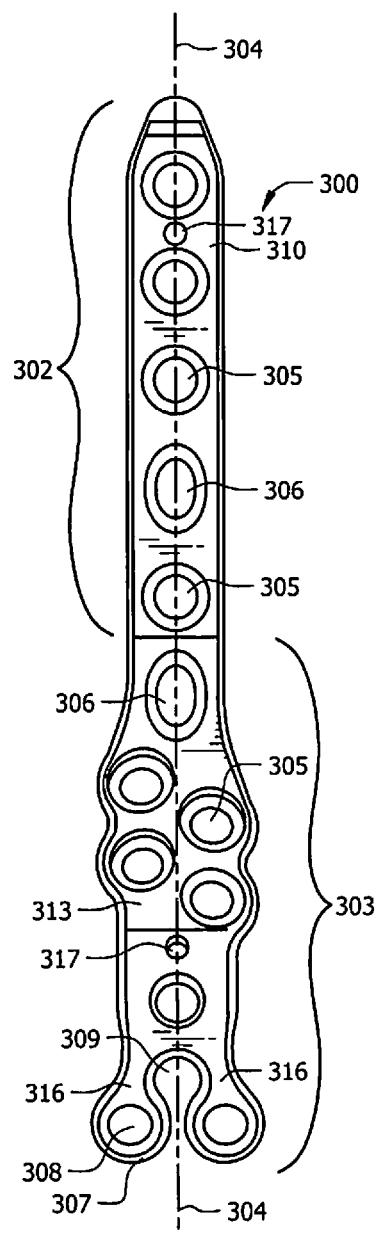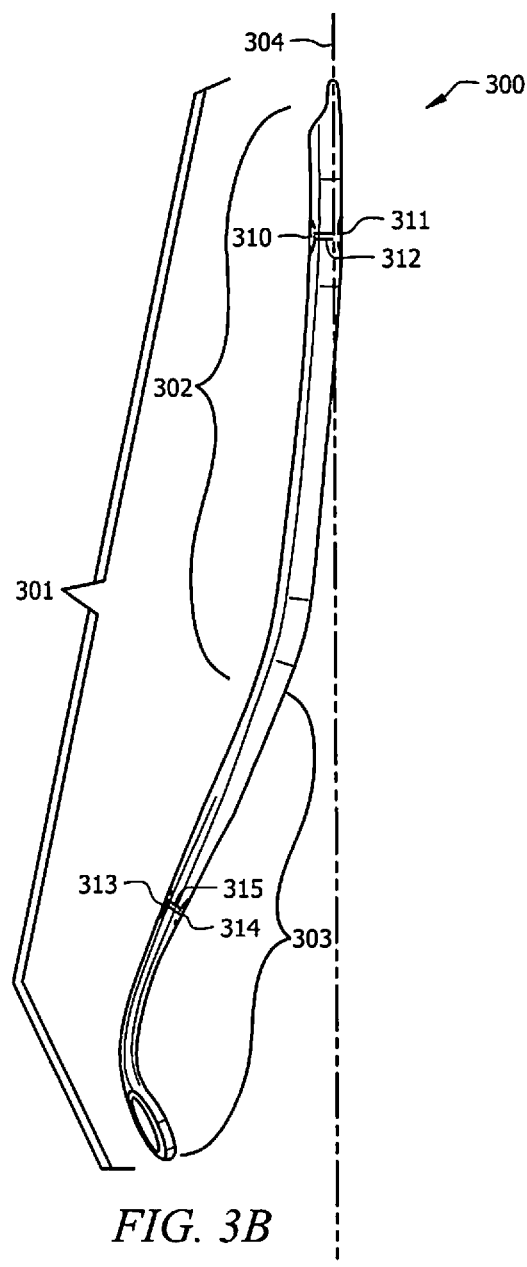
FIG. 3A
FIG. 3B

ANKLE TIBIA PLATES

TECHNICAL FIELD

The present application relates to implant devices for the internal fixation of fractured bones, and more particularly to ankle plates disposed on the tibia.

BACKGROUND

A fractured or broken ankle can include a break or fracture of the tibia bone. Fractures or breaks of the tibia bone are often repaired by holding bone fragments together to achieve fusion. Generally, this is accomplished by the use of ankle plates that are attached directly to the outer surface of the bone via a surgical procedure.

As with any other bone fracture, the structural strength of a plate used to repair an ankle fracture is of paramount importance. Strength of a plate is generally proportional to the thickness of the plate. However, a thick plate often causes discomfort to the patient since is attached directly to the outer surface of the bone under the skin. A thin plate, while possibly being more comfortable for the patient, reduces the structural strength of the plate, thus making it weaker. A weaker ankle plate is more likely to fail under the stress of patient activity, and therefore exposes the patient to serious injury.

The current state of the art favors a "one size fits all" solution for ankle plates. Thus, where a particular ankle plate might not fit a particular patient, a surgeon wishing to modify the ankle plate to fit it to the patient will typically have to bend, shape, cut, thin out, or otherwise manipulate the ankle plate so that it fits the patient. Such modifications to the ankle plate, however, result in a reduction in the structural strength of the ankle plate.

Accordingly, a need exists for an ankle plate that can provide high structural strength, while at the same time providing more options for customization, and reducing discomfort to the patient.

BRIEF SUMMARY

The present application describes various embodiments of an implant device for fusing bones of a fractured tibia. In accordance with one or more embodiments of the present disclosure, an ankle plate may include an L-shaped body. The L-shaped body may include a proximal portion defining a longitudinal axis and a distal portion defining a traverse axis. The L-shaped body may also include a plurality of apertures. Each of the plurality of apertures of the elongated body may be disposed in a manner so as to receive and orient a respective bone fastener in a predetermined direction. In some embodiments of the present disclosure, the apertures may be non-threaded, threaded, or a combination thereof.

In some embodiments, the proximal portion of the L-shaped body may have a first thickness that may be determined by one or more factors such as the size of the tibia, required strength, or other patient-specific requirements. The distal portion of the L-shaped body may have a second thickness that may be determined by a number of factors such as the size of the tibia, required strength, or other patient-specific requirements. In some embodiments of the present disclosure, the distal portion's thickness may be the same as the proximal portion's thickness. Alternatively, the distal portion's thickness may be less than the proximal portion's thickness. Further, the thickness of the L-shaped body may transition from a first thickness of the proximal portion into a second thickness of the distal portion along the longitudinal axis of the proximal portion. In some embodiments of the present disclosure, the transition from the proximal portion's thickness into the distal portion's thickness may be a tapering of the thickness, or it may not be tapered. The distal portion of the L-shaped body may be configured to conform to a distal portion of a tibia bone. For example, the distal portion may include a preformed arc configured to curve with respect to the traverse axis.

The ankle plate according to one or more embodiments of the present disclosure may also include a support bridge. The support bridge may be connected or span between the proximal portion and the distal portion of the L-shaped body. The support bridge may also include a plurality of apertures. Each of the plurality of apertures of the support bridge may be disposed to orient a respective bone fastener into a bone. In some embodiments of the present disclosure, the apertures may be non-threaded, threaded, or a combination thereof. The support bridge may be disposed to provide additional structural support for the ankle plate. Additionally or alternatively, the support bridge may be disposed to provide additional fixation points for the ankle plate. By providing additional structural support and additional fixation points for the ankle plate, the support bridge enables portions of the L-shaped body to be thinned out, while maintaining a high level of overall structural strength for the ankle plate. For example, the thickness of the distal portion may be reduced significantly, thereby lessening the discomfort to the patient, and the loss of structural strength of the ankle plate caused by the thinning of the distal portion may be offset by the gain in structural strength provided by the support bridge.

In accordance with another embodiment of the present disclosure, an ankle plate may include an elongated first portion, and a second portion that may be triangularly shaped and may widen outward with respect to the elongated portion. The elongated first portion and the second portion may include a plurality of apertures. Each of the plurality of apertures of the elongated first portion may be disposed in a manner so as to receive and orient a respective bone fastener in a predetermined direction. In some embodiments of the present disclosure, the apertures may be non-threaded, threaded, or a combination thereof. The elongated first portion may have a first thickness that may be determined by a number of factors such as the size of the tibia, required strength, or other patient-specific requirements. Additionally, or alternatively, the second portion may have a thickness that may be determined by a number of factors such as the size of the tibia, required strength, or other patient-specific requirements. In some embodiments of the present disclosure, the second portion's thickness may be the same as the elongated first portion's thickness. In some embodiments of the present disclosure, the second portion's thickness may be less than the elongated first portion's thickness. The thickness of the elongated first portion may transition into the thickness of the second portion at a point proximate to the point where the elongated first portion transitions into the second portion, or at any point along the elongated first portion, or along the second portion. In some embodiments of the present disclosure, the transition from the thickness of the elongated first portion into the thickness of the second portion may be a tapering of the thickness, or it may not be tapered. Additionally, in some embodiments, the second portion may be configured to conform to a distal portion of a tibia bone.

The ankle plate according to one or more embodiments of the present disclosure may also include a plurality of removable tabs that may be attached to the second portion along the outer edge of the second portion. The removable tabs may be configured to be completely removed from the ankle plate, or may be configured to be flexible and bendable, allowing them to be bent and wrapped around the distal portion of the anterior surface of the tibia bone in order to customize the load bearing support of the ankle plate. The removable tabs may provide additional fixation points for the ankle plate. The additional fixation points provided by the removable tabs may include at least one aperture disposed in a manner so as to receive and orient a respective bone fastener in a predetermined direction.

Additionally, or alternatively, in some embodiments of the present disclosure, the second portion may include a central opening. The central opening may follow the contour of the outer edge of the second portion, and may include a middle bridge disposed within the central opening. Additionally, the middle bridge may be configured to provide additional fixation points for the ankle plate. The additional fixation points provided by the middle bridge may include at least one aperture disposed in a manner so as to receive and orient a respective bone fastener in a predetermined direction. Further, the middle bridge may provide additional structural strength to the ankle plate such that the thickness of the elongated first portion and the thickness of the second portion of the ankle plate may be reduced without reducing the overall structural strength of the ankle plate.

In another embodiment, an ankle plate may include an elongated shaft. The elongated shaft may define a longitudinal axis and may have a proximal portion and a distal portion. The elongated shaft may include a plurality of apertures. Each of the plurality of apertures of the elongated shaft may be disposed to orient a respective bone fastener into a bone. The apertures may be non-threaded, threaded, or a combination thereof. In some embodiments, at least one aperture may be an elongate compression slot. In some embodiments of the present disclosure, the distal portion may be configured to extend proximate to a base of a medial malleolus portion of the tibia. Additionally, or alternatively, the distal portion may have a curvature with respect to the longitudinal axis, and may be configured to conform to a the medial malleolus portion of the distal medial surface of the tibia bone. The proximal portion may have a first thickness and the distal portion may have a second thickness. The thickness of the proximal portion and the thickness of the distal portion may be determined by a number of factors such as the size of the tibia, required strength, or other patient-specific requirements. In some embodiments, the distal portion's thickness may be less than the proximal portion's thickness. The thickness of the proximal portion may transition into the thickness of the distal portion at a point proximate to the point where the proximal portion transitions into the distal portion, or at any point along the proximal portion, or along the distal portion. In some embodiments, the transition from the proximal portion's thickness into the distal portion's thickness may be a tapering of the thickness, or it may not be tapered.

Additionally, in one embodiment, the distal portion of the elongated shaft may include a plurality of removable tabs. Each tab in the plurality of removable tabs may have an aperture disposed in a manner so as to receive and orient a respective bone fastener in a predetermined direction. The apertures may be non-threaded, threaded, or a combination thereof. In some embodiments, the removable tabs may be disposed to define an opening, between the removable tabs. This opening may be utilized as an aperture configured to receive and orient a bone fastener in a predetermined direction into the bone. I will be appreciated that the angles of orientation of the opening aperture may vary according to the requirements of the ankle plate. In some embodiments, the angle of orientation of the opening aperture may be different than the angle of orientation of the tab aperture.

The foregoing has outlined rather broadly the features and technical advantages of the present invention in order that the detailed description that follows may be better understood. Additional features and advantages will be described hereinafter which form the subject of the claims. It should be appreciated by those skilled in the art that the conception and specific embodiment disclosed may be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of embodiments described herein, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present embodiments

BRIEF DESCRIPTION OF THE DRAWINGS

For a more complete understanding, reference is now made to the following descriptions taken in conjunction with the accompanying drawings, in which:

FIGS. 3A and 3B illustrate an example embodiment of a medial ankle plate; and

DETAILED DESCRIPTION

Figure 1A:
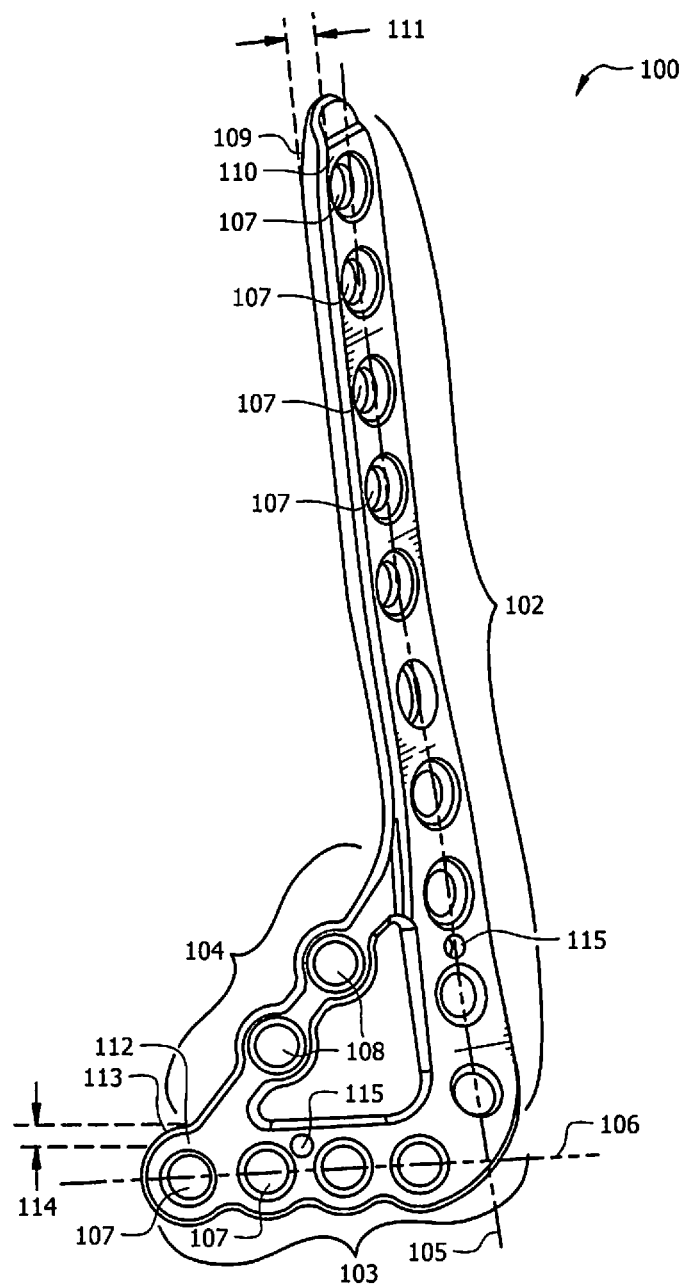
FIG. 1A illustrates an example embodiment of an anterolateral ankle plate.

The detailed description set forth below, in connection with the appended drawings, is intended as a description of various configurations and is not intended to limit the scope of the disclosure. Rather, the detailed description includes specific details for the purpose of providing a thorough understanding of the inventive subject matter. It will be apparent to those skilled in the art that these specific details are not required in every case and that, in some instances, well-known structures and components are shown in block diagram form for clarity of presentation. Likewise, the terminology used herein is for the purpose of describing particular embodiments only, and is not intended to limit the invention Referring to FIG. 1A, an illustrative embodiment of an ankle plate for attaching to the anterior lateral surface of a tibia bone is shown and designated 100. FIG. 1B shows a representative example of ankle plate 100 attached to tibia bone 120. In the illustrated embodiments, ankle plate 100 includes a proximal portion 102 with a longitudinal axis 105, a distal portion 103 with a traverse axis 106, and a support bridge 104.

Proximal portion 102 and distal portion 103 may also be provided with a plurality of apertures 107. The number of apertures 107 in proximal portion 102 and distal portion 103 may generally be dictated by the length of proximal portion 102 and distal portion 103, which may vary depending on the length of tibia bone, the length of the bone fracture being treated, the stability required, or any factors needed to provide efficient fixation strength for the ankle plate. Each aperture 107 may be a threaded aperture or a non-threaded aperture. In some embodiments, some apertures 107 may be threaded while other apertures 107 may be non-threaded. Generally, threaded apertures provide for fixation of ankle plate 100 to tibia bone 120 by use of fixation screws. The apertures 107 may even alternate between threaded and non-threaded, depending on the requirements of the ankle plate. As shown in FIG. 1C, apertures 107 of proximal portion 102 and distal portion 103 may be disposed to receive and orient a bone fastener 130 into the tibia bone. The bone fastener may be a bolt, screw, wire, or any other fastener adapted to secure the ankle plate to the tibia bone. Proximal portion 102 and distal portion 103 may also include temporary guide pin holes 115. In some embodiments, temporary guide pin holes 115 may be adapted to receive and orient a temporary pin that may be used to temporarily hold ankle plate 100 in place while it is being installed on tibia bone 120.

Figure 1B:
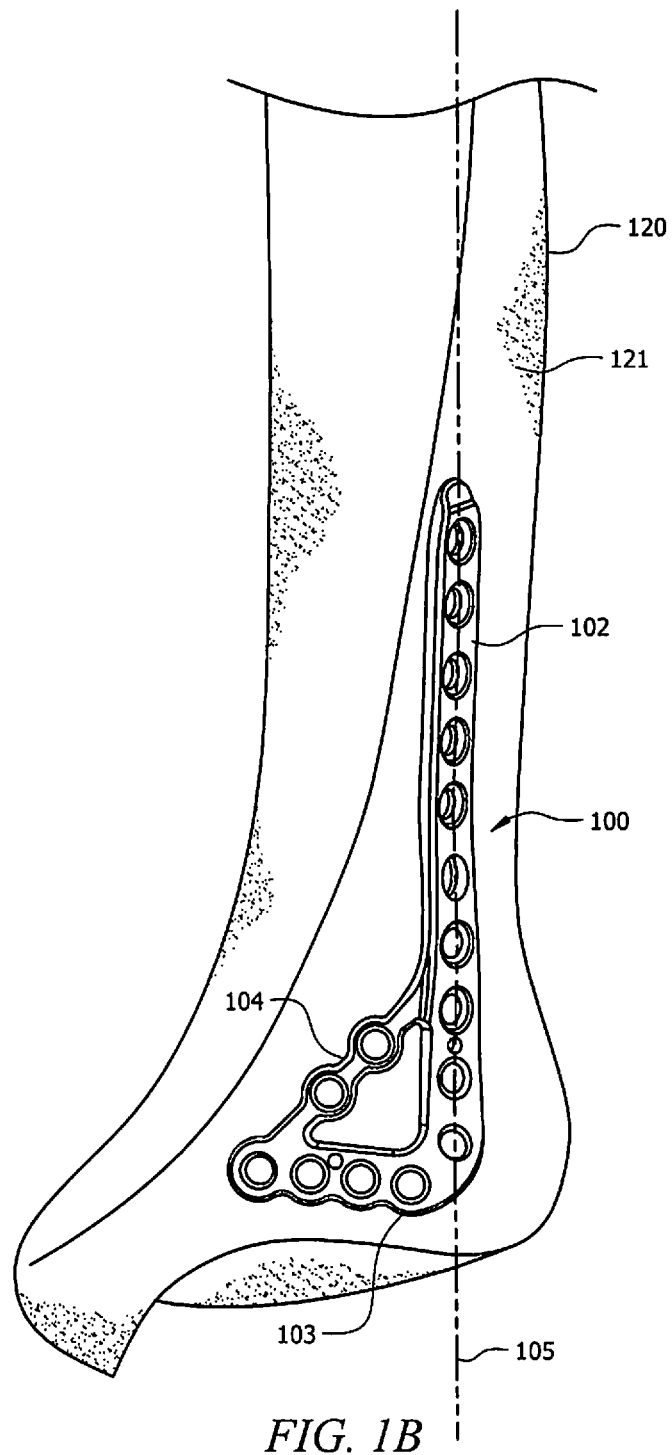
FIGS. 1B and 1C illustrate an example embodiment of an anterolateral ankle plate attached to the anterior lateral surface of a tibia bone.
Figure 1C:
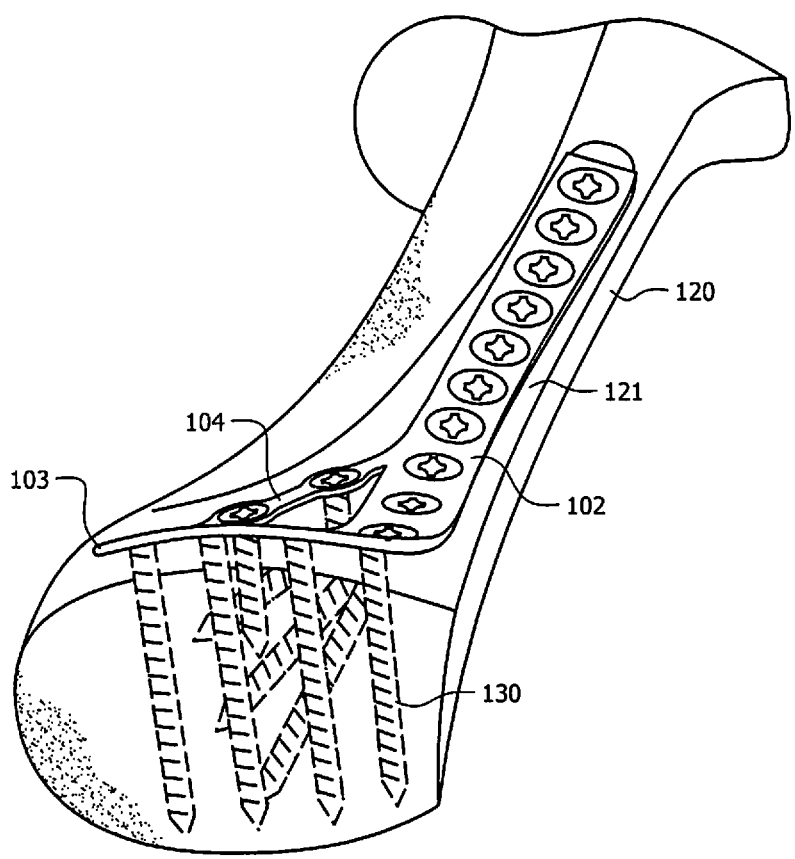

As shown in FIG. 1A, proximal portion 102 may be twisted about longitudinal axis 105 in order to match the anterior lateral bone surface of the tibia. The degree of the twist may be determined by any number of factors, including the geometry of the tibia bone, the fracture being treated, the particular position of the ankle plate on the tibia, and the like. Proximal portion 102 may have a particular length, which may vary depending on the length of tibia bone, the length of the fracture being treated, the stability required, or any factors needed to provide efficient fixation strength for ankle plate 100. As can be seen in FIG. 1A, one end of proximal portion 102 may transition into distal portion 103.

Proximal portion 102 may have a bottom surface 109, and a top surface 110, where the top surface 110 is the surface opposite to bottom surface 109. In this manner, proximal portion 102 may define a thickness 111 which may be the distance between bottom surface 109 and top surface 110. Thickness 111 of proximal portion 102 may be constant over the length of proximal portion 102, or may vary over the length. In some embodiments, the variance of thickness 111 over the length of proximal portion 102 may be uniform, giving proximal portion 102 a tapered shape. Alternatively, thickness 111 may vary non-uniformly over the length of proximal portion 102 in order to conform to a particular shape, or to meet specific patient requirements. In some embodiments, thickness 111 of proximal portion 102 may be constant over the majority of the length of proximal portion 102 but then begin to vary at the point where proximal portion 102 transitions into distal portion 103. As illustrated in the embodiment of FIG. 1A, thickness 111 begins to vary along longitudinal axis 105 after the fifth aperture 107, and transitions from a first thickness 111 to a second thickness 114.

As further shown in FIG. 1A, a distal portion 103 may be provided defining a traverse axis. As shown in FIG. 1C, distal portion 102 may have an arc with respect to axis 106 to match the distal surface of anterior lateral surface 121 of tibia bone 120. The degree of the arc of distal portion 103 may be determined by any number of factors, including the geometry of the tibia bone, the fracture being treated, or the particular position of the ankle plate on tibia bone 120.

Distal portion 103 may have a top surface 112, and a bottom surface 113, where the top surface 112 is the surface opposite to bottom surface 113. In this manner, distal portion 103 may define a thickness 114, which may be the distance between bottom surface 113 and top surface 112. Thickness 114 of distal portion 103 may be constant over the whole length of distal portion 103, or may vary over the length. In some embodiments, the variance of thickness 114 over the length of distal portion 103 may be uniform, giving distal portion 103 a tapered shape. Alternatively, thickness 114 may vary non-uniformly over the length of distal portion 103 in order to conform to a particular shape of the distal surface, or to meet specific patient requirements. In some embodiments, thickness 114 of distal portion 103 may be constant over the majority of the length of distal portion 103 but vary at the point where proximal portion 102 transitions into distal portion 103, thereby tapering the transition between proximal portion 102 and distal portion 103.

In some embodiments of ankle plate 100, thickness 114 of distal portion 103 may be less than thickness 111 of proximal portion 102 in order to accommodate the geometry of anterior lateral portion 121 of tibia bone 120. It should be appreciated that the distal surface of anterior lateral portion 121 may be more prominent under the skin than the rest of anterior lateral surface 121. Accordingly, it may be more desirable to adapt distal portion 103 to have a thickness 114 that is less than thickness 111 of proximal portion 102, in order that ankle plate 100 may not be overly prominent under the skin. In some embodiments, thickness 111 is not constant over the length of proximal portion 102. As can be seen in FIG. 1A, thickness 111 of proximal portion 102 is less at a point proximate to distal portion 103 than at a point at the other end of proximal portion 102. In the illustrated embodiment, thickness 111 begins to decrease at the point where support bridge 104 connects to proximal portion 102, and transitions into thickness 114. In this case, thickness 111 at the point proximate to distal portion 103 may be the same as thickness 114, but may be greater at the point at the other end of proximal portion 102.

It should be appreciated that thickness 111 of proximal portion 102, along with thickness 114 of distal portion 103, may contribute to the overall structural strength of ankle plate 100. Ankle plate structural strength is important because an ankle plate according to embodiments of the present invention may be used to hold pieces of tibia bone 120 together, or even the tibia bone to another bone, in order to stabilize the bone, keep the pieces of bone in alignment next to one another, and thereby enabling the bone fracture to heal. A thicker ankle plate 100 may provide greater structural strength than would a thinner ankle plate 100, and thereby provide better stabilization. However, since ankle plate 100 may be designed to be attached to the anterior lateral surface of a tibia under the skin, a thicker plate may cause more discomfort to the patient than would a thinner plate. Therefore, embodiments may balance the thickness of an ankle plate with the structural strength requirements of the patient in order to design an ankle plate that will cause the least discomfort to the patient while maintaining an appropriate level of structural strength.

As shown in FIG. 1A, ankle plate 100 may include a support bridge 104. Support bridge 104 may be connected between proximal portion 102 and distal portion 103, and may be adapted to provide additional structural support to ankle plate 100. By providing additional structural support to ankle plate 100, support bridge 104 enables proximal portion 102 and distal portion 103 to be thinned, while maintaining a high level of overall structural strength of ankle plate 100. For example, thickness 114 of distal portion 103 may be reduced significantly, thereby lessening the discomfort to the patient, and the loss of structural strength of ankle plate 100 caused by the thinning of distal portion 103 may be offset by the gain in structural strength provided by support bridge 104.

In some embodiments, support bridge 104 may be connected between proximal portion 102 and distal portion 103 at any point along proximal portion 102 and distal portion 103, according to desired structural parameters. The length of support bridge 104 is determined by the distance between the points on proximal portion 102 and distal portion 103 to which support bridge 104 is connected. It is appreciated that a longer support bridge 104 may provide more structural support than a shorter support bridge 104 would. Therefore, the length of support bridge 104 may be selected according to structural strength requirements. For example, thickness 114 of distal portion 103 may be reduced slightly, thereby requiring a relatively short support bridge 104. Alternatively, thickness 114 of distal portion 103 may be reduced further, thereby requiring a longer support bridge 104 to offset the loss of structural strength of ankle plate 100.

Support bridge 104 may have a thickness, which can vary according to desired structural parameters. It is appreciated that a thicker support bridge 104 may provide more structural support than a thinner support bridge 104 would. Therefore, the thickness of support bridge 104 may be selected according to structural strength requirements. For example, thickness 114 of distal portion 103 may be reduced slightly, thereby requiring a relatively thin support bridge 104. Alternatively, thickness 114 of distal portion 103 may be reduced further, thereby requiring a thicker support bridge 104 to offset the loss of structural strength of ankle plate 100. As shown in FIG. 1A, proximal portion 102 has first thickness, distal portion 103 has second thickness, and support bridge 104 has second thickness, although in some embodiments, support bridge may have third thickness. As can be seen, the thickness of support bridge may be less than the thickness of proximal portion 102 at the point where support bridge 104 adjoins proximal portion 102.

One of ordinary skill in the art will appreciate that a loss of structural strength of ankle plate 100 due to a reduction of thickness 111 of proximal portion 102, or thickness 114 of distal portion 103, may be offset by either increasing the length or thickness of support bridge 104, or both.

In some embodiments, support bridge 104 may also be adapted to provide additional fixation points for ankle plate 100. As can be seen in FIGS. 1A and 1B, support bridge 104 is provided with apertures 108. Apertures 108 of support bridge 107 may be adapted to orient a bone fastener into the tibia bone. Ankle plate 100 may be configured so that when ankle plate 100 is attached to the anterior lateral portion of tibia bone 120, support bridge 104 may contact the anterior portion of tibia bone 120. By providing additional fixation points, support bridge 104 provides an increase in stabilization of the fracture area, and may allow insertion of screws that may be used to hold pieces of the fractured tibia bone 120 together.

The number of apertures 108 in the support bridge 104 may generally be dictated by the length of support bridge 104. Each aperture 108 may be a threaded aperture or a non-threaded aperture. In some embodiments, some apertures 108 may be threaded while other apertures 108 may be non-threaded. The apertures 108 may even alternate between threaded and non-threaded, depending on the requirements of the ankle plate. The apertures 108 of support bridge 104 may serve to orient a bone fastener into the tibia bone. The bone fastener may be a bolt, screw, wire, or any other fastener adapted to secure the ankle plate to the tibia bone before, during, or after implantation of ankle plate 100.

In some embodiments, support bridge 104 may be a component separate from proximal portion 102 and distal portion 103 that can be connected to proximal portion 102 and distal portion 103. In that case, support bridge 104 may include a mechanism for connecting between proximal portion 102 and distal portion 103. In other embodiments, support bridge 104 is manufactured as part of proximal portion 102 and distal portion 103, and not as a separate component. In that case, there may be no need to provide a connection mechanism, since support bridge 104, proximal portion 102, and distal portion 103 may be part of a single piece. In some embodiments, support bridge 104 may be removable when the additional support is not needed.

FIGS. 1B and 1C illustrate ankle plate 100 being used on ankle 120. As can be seen in FIG. 1B, ankle plate 100 may be adapted to conform to anterior lateral surface 121 of tibia bone 120. In some embodiments, proximal portion 102 of ankle plate 100 may be adapted to conform to anterior lateral surface 121 of tibia bone 120. In some embodiments, proximal portion 102 may be twisted about longitudinal axis 105 in order to match the contour of anterior lateral surface 121. As will be appreciated, the degree of twist may be determined by the contour of anterior lateral surface 121. In some embodiments, distal portion 103 may be adapted to conform to the distal surface of anterior lateral surface 121 of tibia bone 120. FIG. 1C shows in greater detail distal portion 130 being adapted to conform to the contour of the distal surface of anterior lateral surface 121. In some embodiments, distal portion may have an arc following the contour of the distal surface of anterior lateral surface 121 portion of tibia bone 120. The degree of the arc of distal portion 103 may be determined by any number of factors, including the geometry of the tibia bone, the fracture being treated, the particular position of the ankle plate on tibia bone 120, etc.

Figure 2A:
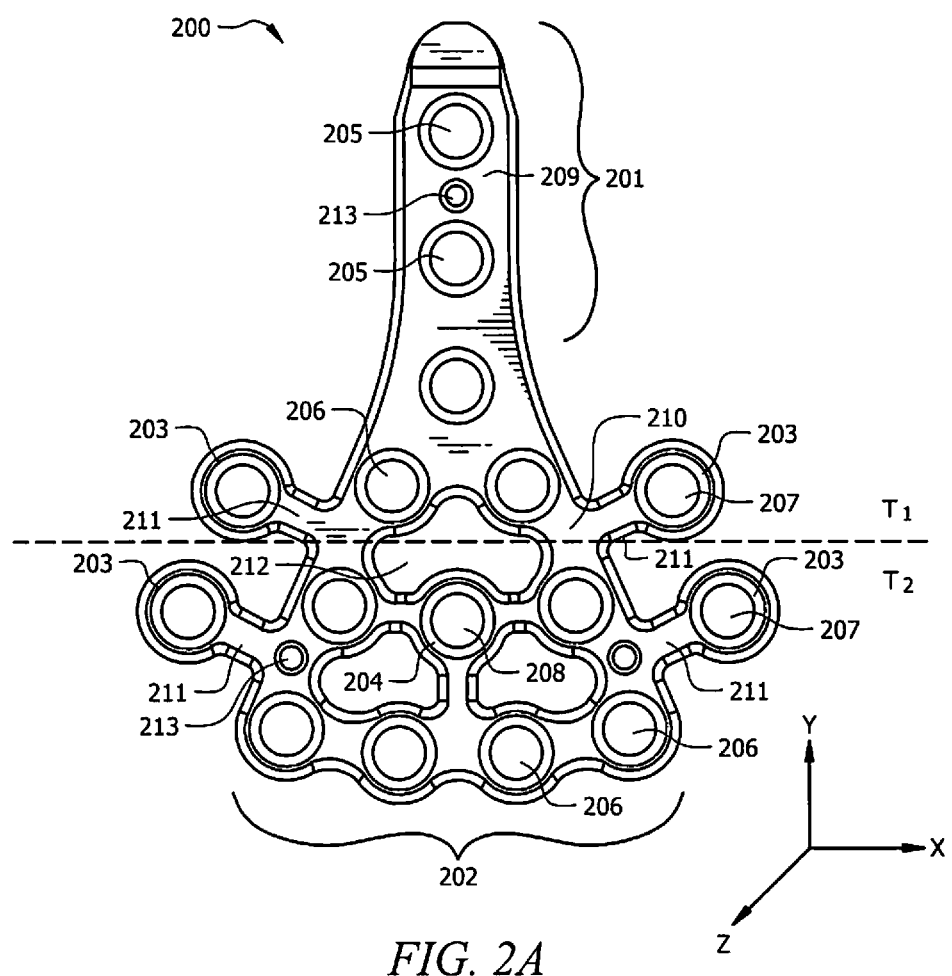
FIG. 2A illustrates an example embodiment of an anterior ankle plate.
Figure 2B:
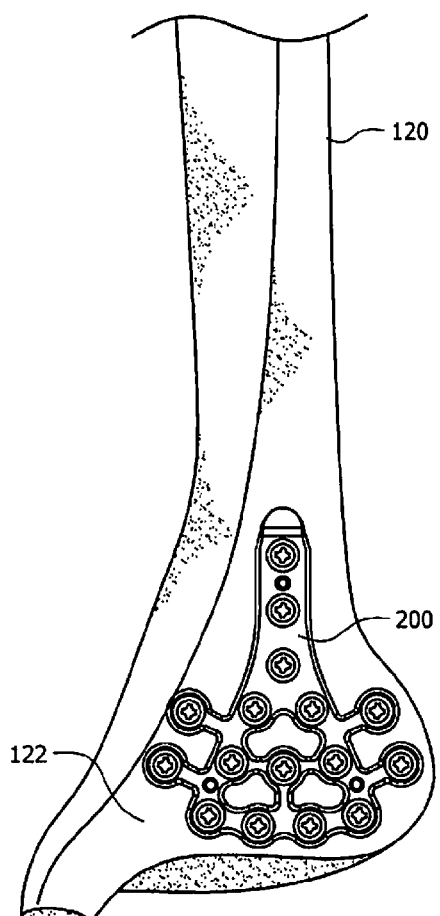
FIGS. 2B-2D illustrate an example embodiment of an anterior ankle plate attached to the anterior surface of a tibia bone.
Figure 2C:
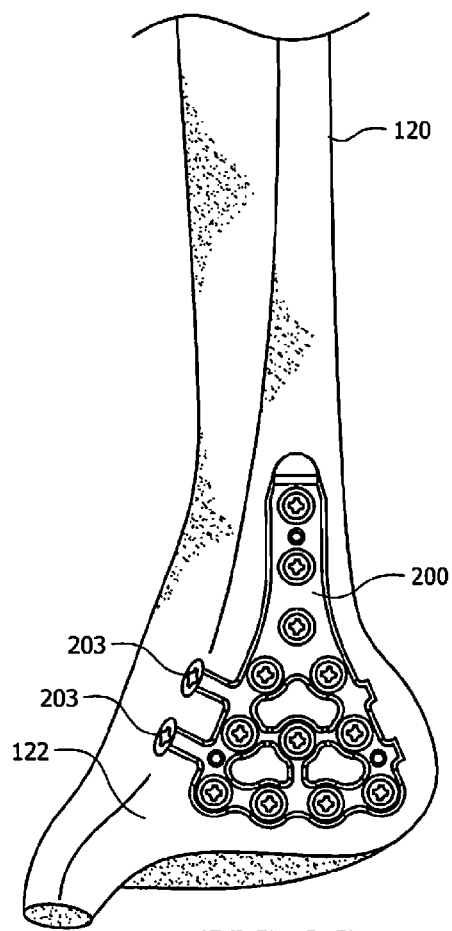

Referring to FIG. 2A, an illustrative embodiment of an ankle plate for attaching to the anterior portion of a tibia bone is shown and designated 200. FIGS. 2B-2C show examples of different configurations of ankle plate 200 attached to tibia bone 120. Referring back to FIG. 2A, in some embodiments, ankle plate 200 may include an elongated first portion 201, a second portion 202, and a removable tabs 203. In some embodiments of ankle plate 200, a middle bridge 204 is provided within central opening 212. Ankle plate 200 may also include temporary guide pin holes 213. In some embodiments, temporary guide pin holes 213 may be adapted to receive and orient a temporary pin that may be used to temporarily hold ankle plate 200 in place while it is being installed on tibia bone 120.

Elongated first portion 201 may have a particular length, which may vary depending on the length of tibia bone, the length of the fracture being treated, the required stability of ankle plate 200, or any factors needed to provide efficient fixation strength for ankle plate 200. As shown in FIG. 2B, in some embodiments, elongated first portion 201 may define a longitudinal axis, and be twisted about the longitudinal axis in order to match the contour of anterior surface 122. As will be appreciated, the degree of twist may be determined by the contour of anterior surface 122.

Elongated first portion 201 may be provided with a plurality of apertures 205. The number of apertures 205 of elongated portion 201 may generally be dictated by the length of elongated portion 201, which may vary depending on the length of tibia bone, the length of the fracture being treated, the stability required, or any factors needed to provide efficient fixation strength for the ankle plate. Each aperture 205 may be a threaded aperture or a non-threaded aperture. In some embodiments, some apertures 205 may be threaded while other apertures 205 may be non-threaded. The apertures 205 may even alternate between threaded and non-threaded, depending on the requirements of the ankle plate. Apertures 205 may serve to orient a bone fastener into the tibia bone. The bone fastener may be a bolt, screw, wire, or any other fastener adapted to secure the ankle plate to the tibia bone before, during, or after implantation of ankle plate 200.

Elongated first portion 201 may have a top surface 209, and a bottom surface (not shown), where the top surface 209 is the surface opposite to the bottom surface. In this manner, elongated first portion 201 may define a first portion thickness which may be the distance between the bottom surface and top surface 209. The first portion thickness may be constant over the whole length of elongated first portion 201, or may vary over the length. In some embodiments, the variance of the first portion thickness over the length of elongated first portion 201 may be uniform, giving elongated first portion 201 a tapered shape. Alternatively, the first portion thickness may vary non-uniformly over the length of elongated first portion 201 in order to conform to a particular shape, or to meet specific patient requirements. In some embodiments, the first portion thickness of elongated first portion 201 may be constant over the majority of the length of elongated first portion 201 but then vary at the point where elongated first portion 201 transitions into second portion 202. Further, the first portion thickness may vary within the second portion. For example, as can be seen in FIG. 2A, approximately 20%-50% of ankle plate 200, which includes the whole length of elongated first portion 201 and part of second portion 202 may have a thickness T1, which transitions into thickness T2 in the lower portion of ankle plate 200.

As shown in FIGS. 2A-2D, second portion 202 may be triangularly shaped, widening outward with respect to elongated portion 201. Second portion 202 may also be adapted to conform to anterior surface 122. For example, second portion 202 may be configured to have a curvature in order to conform to the contour of the distal surface of anterior surface 122 of tibia bone 120. The degree of the curvature of second portion 202 may be determined by any number of factors, including the geometry of the tibia bone, the fracture being treated, or the particular position of the ankle plate on tibia bone 120.

Second portion 202 may be provided with a plurality of apertures 206. The number of apertures 206 of second portion 202 may generally be dictated by the length and width of second portion 202, which may vary depending on the length of tibia bone, the length of the fracture being treated, the stability required, or any factors needed to provide efficient fixation strength for the ankle plate. Each aperture 206 may be a threaded aperture or a non-threaded aperture. In some embodiments, some apertures 206 may be threaded while other apertures 206 may be non-threaded. The apertures 206 may even alternate between threaded and non-threaded, depending on the requirements of the ankle plate. Apertures 206 may serve to orient a bone fastener into the tibia bone. The bone fastener may be a bolt, screw, wire, or any other fastener adapted to secure the ankle plate to the tibia bone before, during, or after implantation of ankle plate 200.

Second portion 202 may have a top surface 210, and a bottom surface (not shown), where the top surface 210 is the surface opposite to the bottom surface. In this manner, second portion 202 may define a second portion thickness which may be the distance between the bottom surface and top surface 210. The second portion thickness may be constant over the whole length of second portion 202, or may vary over the length. In some embodiments, the variance of the second portion thickness over the length of second portion 202 may be uniform, giving second portion 202 a tapered shape. Alternatively, the second portion thickness may vary non-uniformly over the length of second portion 202 in order to conform to a particular shape, or to meet specific patient requirements. In some embodiments, the second portion thickness of second portion 202 may be constant over the majority of the length of second portion 202 but then vary at the point where elongated first portion 201 transitions into second portion 202.

In some embodiments of ankle plate 200, the thickness of second portion 202 may be less than the thickness of elongated first portion 201 in order to accommodate the geometry of anterior portion 122 of tibia bone 120. It should be appreciated that the distal surface of anterior portion 122 may be more prominent under the skin than the rest of anterior surface 122. Accordingly, it may be more desirable to adapt second portion 202 to have a second portion thickness that is less than the first portion thickness of elongated first portion 201, in order that ankle plate 200 may not be overly prominent under the skin.

It should be appreciated that first portion thickness of first portion 201, along with second portion thickness of second portion 202, may contribute to the overall structural strength of ankle plate 200. Ankle plate structural strength is important because an ankle plate according to embodiments of the present invention may be used to hold pieces of tibia bone 120 together, or even the tibia bone to another bone, in order to stabilize the bone, keep the pieces of bone in alignment next to one another, and thereby enabling the bone fracture to heal. A thicker ankle plate 200 may provide greater structural strength than would a thinner ankle plate 200, and thereby provide better stabilization. However, since ankle plate 200 may be designed to be attached to the anterior surface of a tibia bone under the skin, a thicker plate may cause more discomfort to the patient than would a thinner plate. Therefore, embodiments may balance the thickness of an ankle plate with the structural strength requirements of the patient in order to design an ankle plate that will cause the least discomfort to the patient while maintaining an appropriate level of structural strength.

Second portion 202 is shown in FIG. 2A-2D including a central opening 212. It should be appreciated that in some embodiments of ankle plate 200, second portion 202 may not include central opening 212. Central opening 212 may be of a particular shape, or it may follow the contour of the outer edge of second portion 202. In some embodiments, central opening 212 of second portion 202 may be adapted to include middle bridge 204, as shown in FIG. 2A. Middle bridge 204 may be adapted to provide additional structural support to ankle plate 200. It should be appreciated that by providing additional structural support to ankle plate 200, middle bridge 204 enables elongated first portion 201 and second portion 202 to be thinned, while maintaining a high level of overall structural strength of ankle plate 200. For example, the second portion thickness of second portion 202 may be reduced significantly, thereby lessening the discomfort to the patient, and the loss of structural strength of ankle plate 200 caused by the thinning of second portion 202 may be offset by the gain in structural strength provided by middle bridge 204.

The size of middle bridge 204 may be determined by the size second portion 202, or the size of central opening 212. It is appreciated that a bigger middle bridge 204 may provide more structural support than a smaller middle bridge 204 would. Therefore, the size of middle bridge 204 may be selected according to structural strength requirements. For example, the second portion thickness of second portion 202 may be reduced slightly, thereby requiring a relatively small middle bridge 204. Alternatively, the second portion thickness of second portion 202 may be reduced further, thereby requiring a bigger middle bridge 204 to offset the loss of structural strength of ankle plate 200.

In some embodiments, middle bridge 204 may be adapted to provide additional fixation points for ankle plate 200. As can be seen in FIGS. 2A-2D, middle bridge 204 is provided with aperture 208. Aperture 208 may be adapted to orient a bone fastener into the tibia bone. By providing additional fixation points, support bridge 104 provides an increase in stabilization of the fracture area, and may allow insertion of screws that may be used to hold pieces of the fractured tibia bone 120 together. Although middle bridge 204 is shown as including one fixation point, the number of apertures 208 in middle bridge 204 may generally be dictated by the size of middle bridge 204. Aperture 208 may be a threaded aperture or a non-threaded aperture. Aperture 208 may be configured to orient a bone fastener into the tibia bone.

As shown in FIG. 2A, ankle plate 200 may include removable tabs 203. In a preferred embodiment of ankle plate 200, removable tabs 203 may be ring-shaped and may be attached to the outer edge of second portion 202 with a bridge 211. Removable tabs 203 may be configured to be completely removed from ankle plate 200. Additionally, removable tabs 203 may be configured to be flexible and bendable at bridge 211, allowing them to be bent and wrapped around the distal portion of the anterior surface of the tibia bone in order to customize the load bearing support of ankle plate 200. In the current embodiment, removable tabs 203 may be pre-formed to curve around the surface of tibia bone 120. Removable tabs 203 may allow a "one-size-fits-all", or universal, ankle plate 200 that may be suitable for patients with different size requirements. For example, where ankle plate 200 is being used for treating a patient with a relatively small tibia bone 120, removable tabs 203 may be removed, or bent and wrapped around the bone to provide fixation points for ankle plate 120. It should be appreciated by those skilled in the art, that providing removable tabs 203 that can bend to wrap around the tibia bone eliminates the need to bend second portion 202 to wrap around the bone. Therefore, a smaller second portion 202 can be provided with removable tabs 203 that can be either removed when not needed, or bent to wrap around the tibia bone to provide additional fixation points.

FIG. 2C, shows a configuration of ankle plate 200 where two removable tabs have been completely removed, in order to facilitate implantation of ankle plate 200. This may be the case where ankle plate 200 is being used to treat a patient with a relatively small tibia bone. Alternatively, FIG. 2B shows a configuration of ankle plate 200 where no tabs have been removed. This may be the case where ankle plate 200 is being used to treat a patient with a larger tibia bone. It should be appreciated that removable tabs 203 may be removed from ankle plate 200 by use of specialized tools, stet generally available tools, that apply a particular amount of force required to remove tabs 203 from ankle plate 200 by fracture of bridge 211, or by bending removable tabs in one direction and then the opposite direction until a fracture of bridge 211 is effected. Preferably, removal of one or more removable tabs 203 is done in a manner so as to not have sharp, or rough edges. In some embodiments, removable tabs 203 may be adapted to facilitate their removal from ankle plate 200. For example, removable tabs 203 may be made of dissimilar materials than second portion 202, or score lines may be provided at bridge 211. Removable tabs 203 may be adapted to fracture from ankle plate 200 upon the application of a particular amount of force.

Figure 2D:
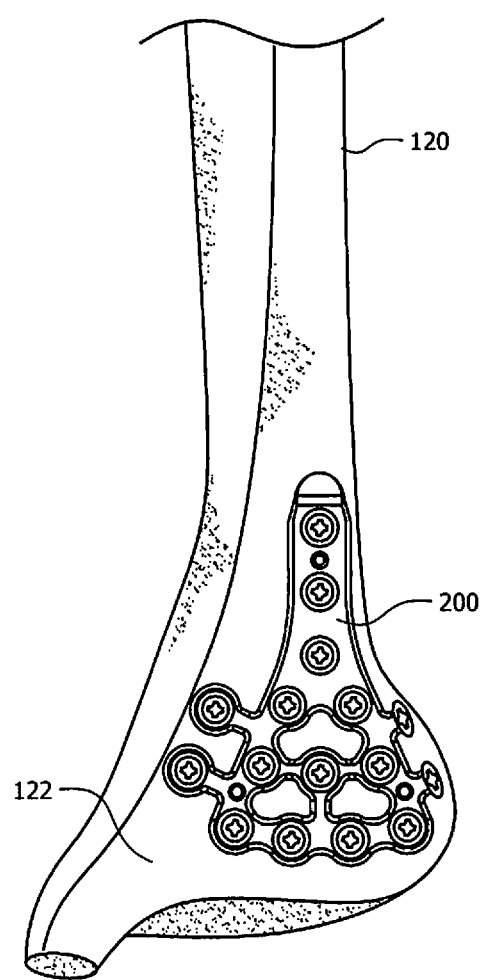

FIGS. 2C and 2D show a configuration of ankle plate 200 where removable tabs 203 have been bent to wrap around anterior surface 122. In some embodiments, removable tabs 203 may be adapted to be flexible and bendable, thereby allowing a surgeon to easily bend them and wrapped them around tibia bone 120 to conform to the contour of anterior surface 122. In a preferred embodiment, bridge 211 of removable tabs 203 may be configured to bend in rotation around the y-axis. Thus, each bridge 211 may have a rectangular cross-section, with a width greater than thickness.

Wrapping removable tabs 203 around anterior surface 122 may provide additional fixation point. In some embodiments, wrapping removable tabs 203 around tibia bone 120 may provide additional angles for fixation of ankle plate 200. For example, by bending removable tabs 203 to a particular angle relative to the planar surface of second portion 202, a fixation point may be provided that may be adapted to orient a bone fastener into tibia bone 120 at the particular angle. To effect bending, specialized bending tools may be provided that apply force proximate to bridge 211 to effect a change in removable tabs 203 orientation. Removable tabs 203 bending may be effected while ankle plate 200 is installed on the bone, or may be effected while ankle plate 200 is not on the bone, prior to surgery. In some embodiments, the area of removable tabs 203 around the aperture 207 may be designed thicker than bridge 211 in order to ensure that aperture 207 is not deformed.

Removable tabs 203 may be adapted to include apertures 207, which may provide additional fixation points for ankle plate 200. By providing additional fixation points, removable tabs 203 may provide an increase in stabilization of the fracture area, and may allow insertion of screws that may be used to hold pieces of the fractured tibia bone 120 together. Each aperture 207 may be implemented in a similar manner as described with respect to apertures 205 and 206.

Referring to FIGS. 3A and 3B, an illustrative embodiment of an ankle plate for attaching to the medial surface of a tibia bone is shown and designated 300. In some embodiments, ankle plate 300 may include an elongated shaft 301, which may define a longitudinal axis 304, a proximal portion 302, and a distal portion 303. Ankle plate 300 may also include temporary guide pin holes 317. In some embodiments, temporary guide pin holes 317 may be adapted to receive and orient a temporary pin that may be used to temporarily hold ankle plate 300 in place while it is being installed on tibia bone 120.

Figure 3C:
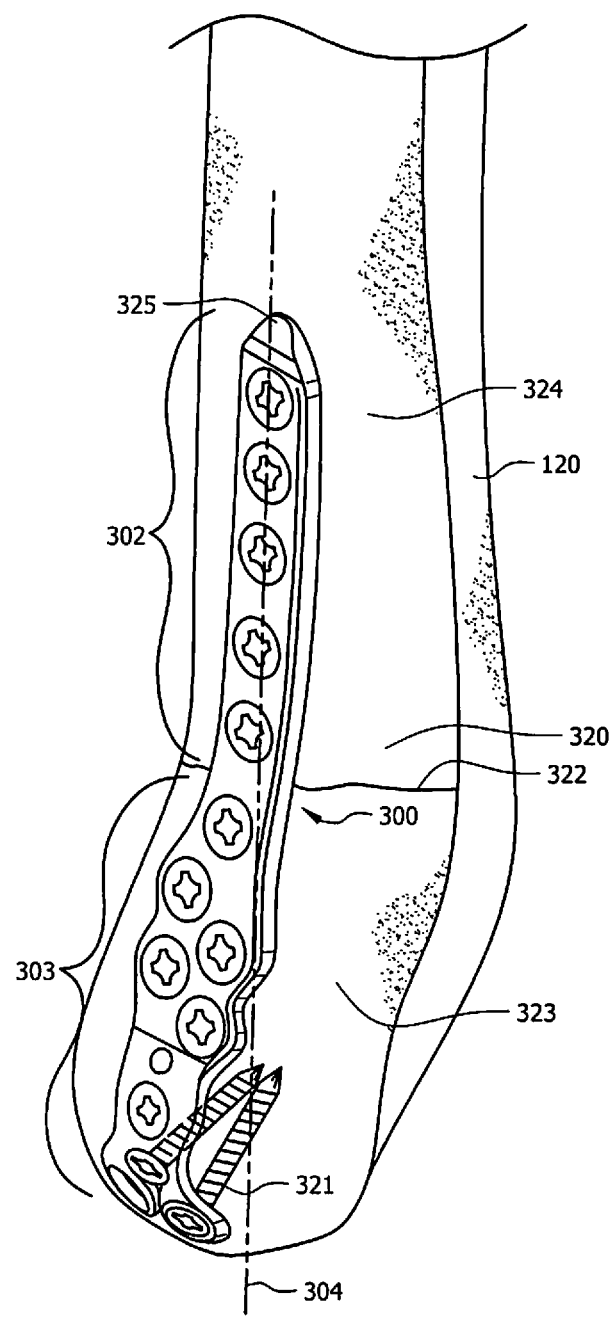
FIG. 3C illustrate an example embodiment of a medial ankle plate attached to the medial surface of a tibia bone.

As can be seen in FIG. 3C, ankle plate 300 may be adapted to conform to medial surface 320 of tibia bone 120. In some embodiments, ankle plate 300 may be configured to define a curvature with respect to longitudinal axis 304 in order to conform to the contour of medial surface 320. The curvature defined by ankle plate 300 may be convex with respect to longitudinal axis 304 along proximal portion 302, and may be concave with respect to longitudinal axis 304 along distal portion 303. The degree of the convex curvature along proximal portion 302 may increase gradually along the length of proximal portion 302. In that case, the degree of the convex curvature along proximal portion 302 at one point in proximal portion 302 may be different than the degree of the convex curvature at another point in proximal portion 302. Similarly, the concave curvature along distal portion 303 may increase gradually along the length of distal portion 303, or may be constant. In should be appreciated that the degree of the convex curvature of proximal portion 302 and the degree of the concave curvature of distal portion 303 may be determined by any number of factors, including the geometry of medial surface 304 of tibia bone 120, the size of the patient being treated, the type of fracture being treated, the particular position of the ankle plate on tibia bone 120, etc.

In some embodiments, the concave curvature along distal portion 303 may be pre-configured to conform to medial malleolus 321. One of ordinary skill in the art will appreciate that the medial malleolus refers to the prominent area of the medial side of tibia bone 120, formed by the lower end of tibia bone 120. Accordingly, in some embodiments, distal portion 303 may be provided having a concave curvature in order to match the contour of medial malleolus 321. The concave curvature of distal portion 303 may be effected during manufacture of ankle plate 300, after manufacture but before surgery, or during surgery before implantation. It should be appreciated that where the convex curvature is effected after manufacture, the structural strength of ankle plate 300 may be reduced due to the curvature. Thus, the pre-curve of ankle plate prevents, or lessens, any weakening that would result from after-manufacturing bending. In some embodiments of the present invention, ankle plate 300 may be provided configured to have sufficient strength such that any weakening experienced from after-manufacture bending will still result in an ankle plate with acceptable strength for implantation.

Referring to FIG. 3B, proximal portion 302 may have a top surface 310, and a bottom surface 311, where top surface 310 is the surface opposite to bottom surface 311. In this manner, proximal portion 302 may define a thickness 312, which may be the distance between bottom surface 311 and top surface 310. Thickness 312 of proximal portion 302 may be constant over the whole length of proximal portion 302, or may vary over the length. In some embodiments, the variance of thickness 312 may be uniform, giving proximal portion 302 a tapered shape. Alternatively, thickness 312 may vary non-uniformly over the length of proximal portion 302 in order to conform to a particular shape of medial surface 320, to meet specific patient requirements, etc. In some embodiments, thickness 312 may be constant over the majority of the length of proximal portion 302 but vary at the point where proximal portion 302 transitions into distal portion 303, thereby tapering the transition between proximal portion 302 and distal portion 303.

The length of distal portion 303 may extend from the distal tip of medial malleolus 321 to diaphyseal-metaphyseal junction 322 of the distal tibia. This allows the apertures of distal portion 303 to be aligned with metaphyseal area 323 for fixation of ankle plate 300. Proximal portion 302 may extend from metaphyseal-diaphyseal junction 322 proximally along diaphyseal area 324 of the tibia bone 120. The length of distal proximal portion 302 may vary depending factors which may include the geometry of the fracture being treated, including size and shape. In some embodiments, the length of proximal portion 302 may be determined such that there are at least three apertures 305 between the proximal end of the fracture being treated and proximal end 325 of proximal portion 302. In some embodiments, the length of proximal portion 302 may span the whole length of diaphyseal area 324 of medial surface 320 of tibia 120.

Proximal portion 302 may be provided with a plurality of apertures 305 and 306. The number of apertures 305 and 306 may generally be dictated by the length of proximal portion 302, which may vary depending on the length of tibia bone 120, the length of the fracture being treated, the stability required, or any factors needed to provide efficient fixation strength for the ankle plate. Each aperture 305 and 306 may be a threaded aperture or a non-threaded aperture. In some embodiments, non-threaded apertures may include elongate compression slots 306 for, and/or threaded apertures 305. In some embodiments, some apertures may be threaded apertures while other apertures may be non-threaded. Apertures 305 and 306 may even alternate between threaded and non-threaded, depending on the requirements of the ankle plate. Apertures 305 and 306 may be adapted to orient a bone fastener into tibia bone 120.

As shown in FIG. 3B, distal portion 303 may have a top surface 313, and a bottom surface 314, where top surface 313 is the surface opposite to bottom surface 314. In this manner, distal portion 303 may define a thickness 315, which may be the distance between bottom surface 314 and top surface 313. Thickness 315 may be constant over the whole length of distal portion 303, or may vary over the length. In some embodiments, the variance of thickness 315 may be uniform, giving distal portion 303 a tapered shape. Alternatively, thickness 315 may vary non-uniformly over the length of distal portion 303 in order to conform to a particular shape of medial surface 320, to meet specific patient requirements, etc. In some embodiments, thickness 315 may be constant over the majority of the length of distal portion 303 but vary at the point where proximal portion 302 transitions into distal portion 303, thereby tapering the transition between proximal portion 302 and distal portion 303.

In some embodiments of ankle plate 300, thickness 315 of distal portion 303 may be less than thickness 311 of proximal portion 302 in order to accommodate the geometry of medial surface 320 of tibia bone 120. It should be appreciated that medial malleolus 321 of medial surface 320 may be more prominent under the skin than the rest of medial surface 320. Accordingly, it may be more desirable to adapt distal portion 303 to have a thickness 315 that is less than thickness 311 of proximal portion 302, so that ankle plate 300 may not be overly prominent under the skin.

As shown in FIG. 3A, distal portion 303 may be configured to include a plurality of apertures 305 and 306. The number of apertures 305 and 306 may generally be dictated by the length of distal portion 303, which may vary depending on the length of tibia bone 120, the length of the fracture being treated, the stability required, or any factors needed to provide efficient fixation strength for the ankle plate. Each aperture 305 and 306 may be a threaded aperture or a non-threaded aperture. In some embodiments, non-threaded apertures may include elongate compression slots 306 for compression screws (not shown), and/or threaded apertures 305. In some embodiments, some apertures may be threaded apertures while other apertures may be non-threaded. Apertures 305 and 306 may even alternate between threaded and non-threaded, depending on the requirements of the ankle plate. In some embodiments, such as the one shown in FIGS. 3A and 3B, apertures 305 and 306, may be aligned to define two rows of apertures. The first and second rows may be approximately parallel and apertures of the second row may be staggered (transverse to longitudinal axis 304) with respect to apertures 305 of the first row. Apertures 305 and 306 may be adapted to orient a bone fastener into tibia bone 120. The bone fastener may be a bolt, screw, wire, or any other fastener adapted to secure the ankle plate to the tibia bone before, during, or after implantation of ankle plate 300.

Distal portion 303 may include removable tabs 307. In a preferred embodiment of ankle plate 300, removable tabs 307 may be ring-shaped and may be attached to the one end distal portion 303 with a bridge 316. In some embodiments of ankle plate 300, removable tabs 307 define one end of distal portion 303. Removable tabs 307 may be configured to be completely removed from ankle plate 300, or may be configured to be flexible and bendable at bridge 316 to extend under the base, or point proximate to the distal portion of medial malleolus 321 (as seen in FIG. 3C), in order to customize the load bearing support of ankle plate 300.

Removable tabs 307 may be removed from ankle plate 300 by use of specialized tools, stet generally available tools, that apply a particular amount of force required to remove tabs 307 from ankle plate 300 by fracture of bridge 316, or by bending removable tabs 307 in one direction and then the opposite direction until a fracture of bridge 316 is effected. Preferably, removal of one or more removable tabs 307 is done in a manner so as to not have sharp, or rough edges. In some embodiments, removable tabs 307 may be adapted to facilitate their removal from ankle plate 300. For example, removable tabs 307 may be made of dissimilar materials than the rest of distal portion 303, or score lines may be provided at bridge 316. Removable tabs 307 may be adapted to fracture from ankle plate 300 upon the application of a particular amount of force.

In some embodiments, removable tabs 307 may be adapted to be bendable, thereby allowing a surgeon to easily bend them and wrapped them around the base of medial malleolus 321 to conform to the contour of medial malleolus 321. To effect bending, specialized bending tools may be provided that apply force proximate to bridge 316 to effect a change in the orientation of removable tabs 307. In some embodiments, the area of removable tabs 307 around aperture 308 may be designed thicker than bridge 316 in order to ensure that aperture 308 is not deformed when bending is effected Bending removable tabs 307 to extend under the base of medial malleolus 321, may provide additional angles for fixation of ankle plate 300. For example, by bending removable tabs 307 to a particular angle relative to the planar surface of distal portion 303, a fixation point may be provided that may be adapted to orient a bone fastener into tibia bone 120 at the particular angle. In some embodiments, this angle may be an acute angle with respect to longitudinal axis 304. Being configured to orient a bone fastener into tibia bone 120 at a particular angle, removable tabs 307 may be used to insert a transfixation screw into the bone fracture.

Removable tabs 203 may be adapted to include apertures 308, which may provide additional fixation points for ankle plate 300. By providing additional fixation points, removable tabs 203 may provide an increase in stabilization of the fracture area, and may allow insertion of screws that may be used to hold pieces of the fractured tibia bone 120 together. Each aperture 207 may be a threaded aperture or a non-threaded aperture. Apertures 207 may be adapted to orient a bone fastener into the tibia bone. The bone fastener may be a bolt, screw, wire, or any other fastener adapted to secure the ankle plate to the tibia bone As can be seen in FIG. 3A, removable tabs 307 may be configured to define opening 309 between each removable tab 307. Opening 309 may be adapted to provide additional fixation point for ankle plate 300. In some embodiments, removable tabs 309 may be designed in such a way so that the space between bridges 316 define an opening 309 that may be adapted to orient a bone fastener into tibia bone 120. Opening 309 may be configured to be a threaded opening or a non-threaded opening. In some embodiments, opening 309 may be adapted to be used when removable tabs 307 are removed.

One or more of the implant devices, or a component thereof, described with reference to FIGS. 1A-1C, 2A-2D, and 3A-3C may be formed using metals (e.g., titanium), polymers, ceramics, glasses, composite materials, biological materials or tissues, insulators, conductors, semiconductors, or other biocompatible or non-biocompatible materials. Different materials may be used for individual components. Different materials may be combined in a single component. In some embodiments, the implant device body may be formed using polyetheretherketone (PEEK), either alone or in combination with other materials. Using PEEK to form the implant device may be beneficial because it approximates a modulus strength of bone. As compressive forces are applied to the bone by the PEEK implant device (or the pressure and friction forces generated by the screws), the bone structures and various tissues and cells react, creating more bony structure. Additionally, using PEEK implant devices may cause bone graft shoots to take more load faster than with titanium implant devices (i.e., because the titanium implant device does not compress the bones as efficiently as the PEEK implant device).

It should be understood that the present system, kits, apparatuses, and methods are not intended to be limited to the particular forms disclosed. Rather, they are to cover all combinations, modifications, equivalents, and alternatives falling within the scope of the claims.

The claims are not to be interpreted as including means-plus- or step-plus-function limitations, unless such a limitation is explicitly recited in a given claim using the phrase(s) "means for" or "step for," respectively.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

In the foregoing Detailed Description, various features are grouped together in several embodiments for the purpose of streamlining the disclosure. This method of disclosure is not to be interpreted as reflecting an intention that the disclosed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

Although the embodiments of the present disclosure and their advantages have been described in detail, it should be understood that various changes, substitutions and alterations can be made herein without departing from the spirit and scope of the disclosure as defined by the appended claims. Moreover, the scope of the present disclosure is not intended to be limited to the particular embodiments of the process, machine, manufacture, composition of matter, means, methods and steps described herein. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An anterolateral tibia plate comprising:
an L-shaped body having a proximal portion defining a longitudinal axis, and a distal portion defining a traverse axis, said L-shaped body including a first plurality of apertures, said first plurality of apertures being disposed to orient a respective bone fastener into a bone, said proximal portion having a first bottom surface and a first top surface, said first bottom surface configured to contact said bone when said anterolateral tibia plate is attached to said bone, a first distance between said first bottom surface and said first top surface defining a first thickness, and said distal portion having a second bottom surface and a second top surface, said second bottom surface configured to contact said bone when said anterolateral tibia plate is attached to said bone, a second distance between said second bottom surface and said second top surface defining a second thickness; and
a support bridge connected between said proximal portion and said distal portion, wherein said support bridge has a first edge and a second edge that are perpendicular to a bottom surface of the support bridge, said bottom surface configured to contact said bone when said anterolateral tibia plate is attached to said bone, a distance between said first edge and second edge defining a support bridge width, wherein said proximal portion has a proximal portion width defined by a distance between a first edge and a second edge of said proximal portion that are perpendicular to said first bottom surface, wherein said support bridge width is smaller than said proximal portion width, and wherein said support bridge has a third thickness that is different than said first thickness and second thickness.

2. The anterolateral tibia plate of claim 1, wherein said support bridge includes at least one aperture, each aperture of said at least one aperture being disposed to orient a respective bone fastener into said bone.

3. The anterolateral tibia plate of claim 1, wherein said second thickness is less than said first thickness.

4. The anterolateral tibia plate of claim 1, wherein at least one aperture in said first plurality of apertures is a threaded aperture.

5. The anterolateral tibia plate of claim 1, wherein said first thickness tapers into said second thickness along the longitudinal axis of the proximal portion.

6. The anterolateral tibia plate of claim 1, wherein said bone is a tibia bone, and wherein said L-shaped body is configured to conform to an anterior lateral portion of said tibia bone.

7. The anterolateral tibia plate of claim 1, wherein said bone is a tibia bone, and wherein said distal portion of said L-shaped body is configured to conform to a distal portion of said tibia bone.

* * * * *